United States Patent [19]
Kensey

[11] Patent Number: 5,061,274
[45] Date of Patent: Oct. 29, 1991

[54] PLUG DEVICE FOR SEALING OPENINGS AND METHOD OF USE

[75] Inventor: Kenneth Kensey, Chester Springs, Pa.

[73] Assignee: Kensey Nash Corporation, Exton, Pa.

[21] Appl. No.: 445,315

[22] Filed: Dec. 4, 1989

[51] Int. Cl.$^5$ ............................................ A61B 17/04
[52] U.S. Cl. .................................... 606/213; 606/215; 604/15
[58] Field of Search ........ 606/213, 215, 216, 228–231; 604/11, 13, 15, 60; 600/32; 623/1, 11; 128/831, 865, 887

[56] References Cited

U.S. PATENT DOCUMENTS

| | | | |
|---|---|---|---|
| 2,934,068 | 4/1960 | Graham, Jr. et al. | 604/15 |
| 3,706,311 | 12/1972 | Kokx et al. | 604/15 |
| 3,874,388 | 4/1975 | King et al. | 623/11 |
| 4,361,151 | 11/1982 | Fitzgerald | 604/15 |
| 4,744,364 | 5/1988 | Kensey | 604/15 |
| 4,852,568 | 8/1989 | Kensey | 606/213 |
| 4,890,612 | 1/1990 | Kensey | 606/213 |

*Primary Examiner*—Stephen C. Pellegrino
*Assistant Examiner*—Ralph A. Lewis
*Attorney, Agent, or Firm*—Caesar, Rivise, Bernstein, Cohen & Pokotilow, Ltd.

[57] ABSTRACT

An instrument and methods of making and use for sealing a small, e.g., percutaneous, incisions or punctures. The instrument in the form of a tubular member having a plug therein. The tubular member includes a proximally located piston and a distally located portion having an open free end for introduction into the incision or puncture. The plug comprises a cord and a thin filament, with the cord being formed of a resorbable material and being folded in two to form an apex portion and a pair of wing portions extending therefrom. The filament is secured to the apex portion. The plug is located within the tubular member so that the apex portion is disposed adjacent the free end and with the wing portions and the filament extending toward the proximally located portion. The plug is then expelled partially from the tubular member so that the apex portion extends through the incision or puncture. The filament is then drawn proximally direction to pull the apex portion into engagement with the free end of the tubular member to expand the apex portion to form a head having a tissue engagement surface. The plug is then drawn back through the incision or puncture so that the tissue engagement surface intimately engages the tissue contiguous with the incision or puncture.

34 Claims, 3 Drawing Sheets

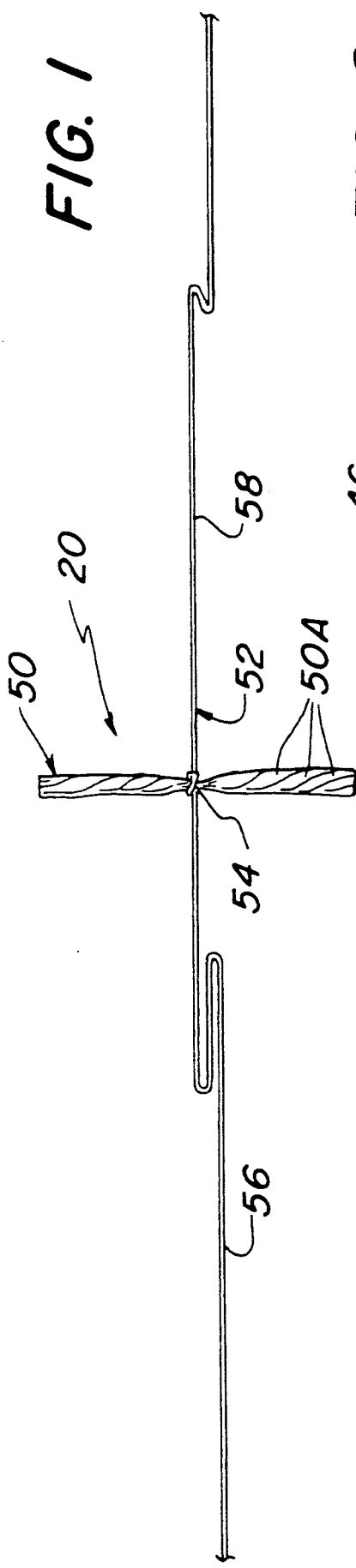
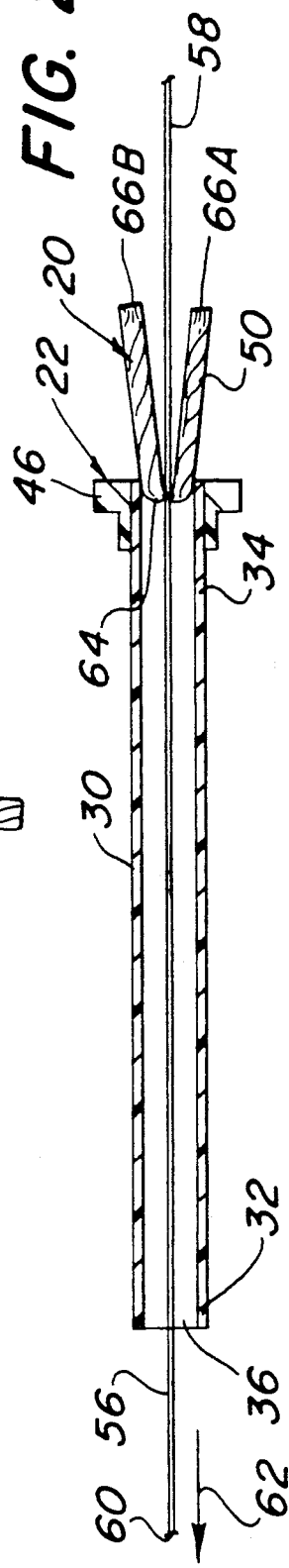
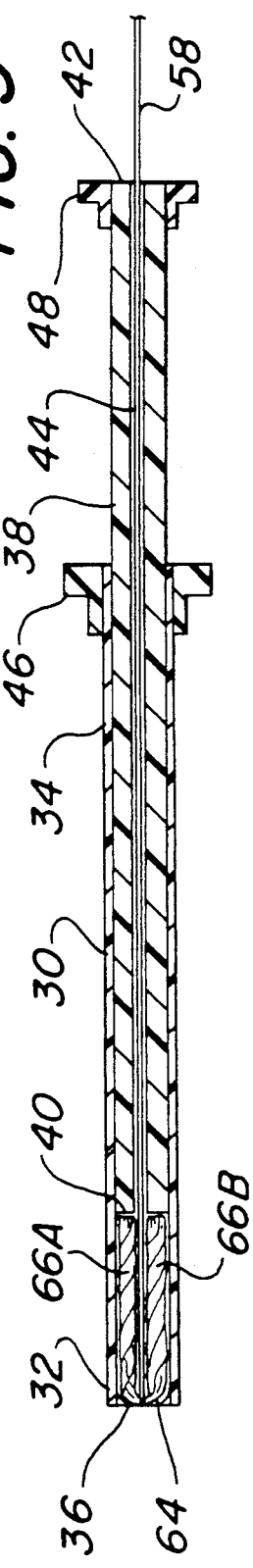

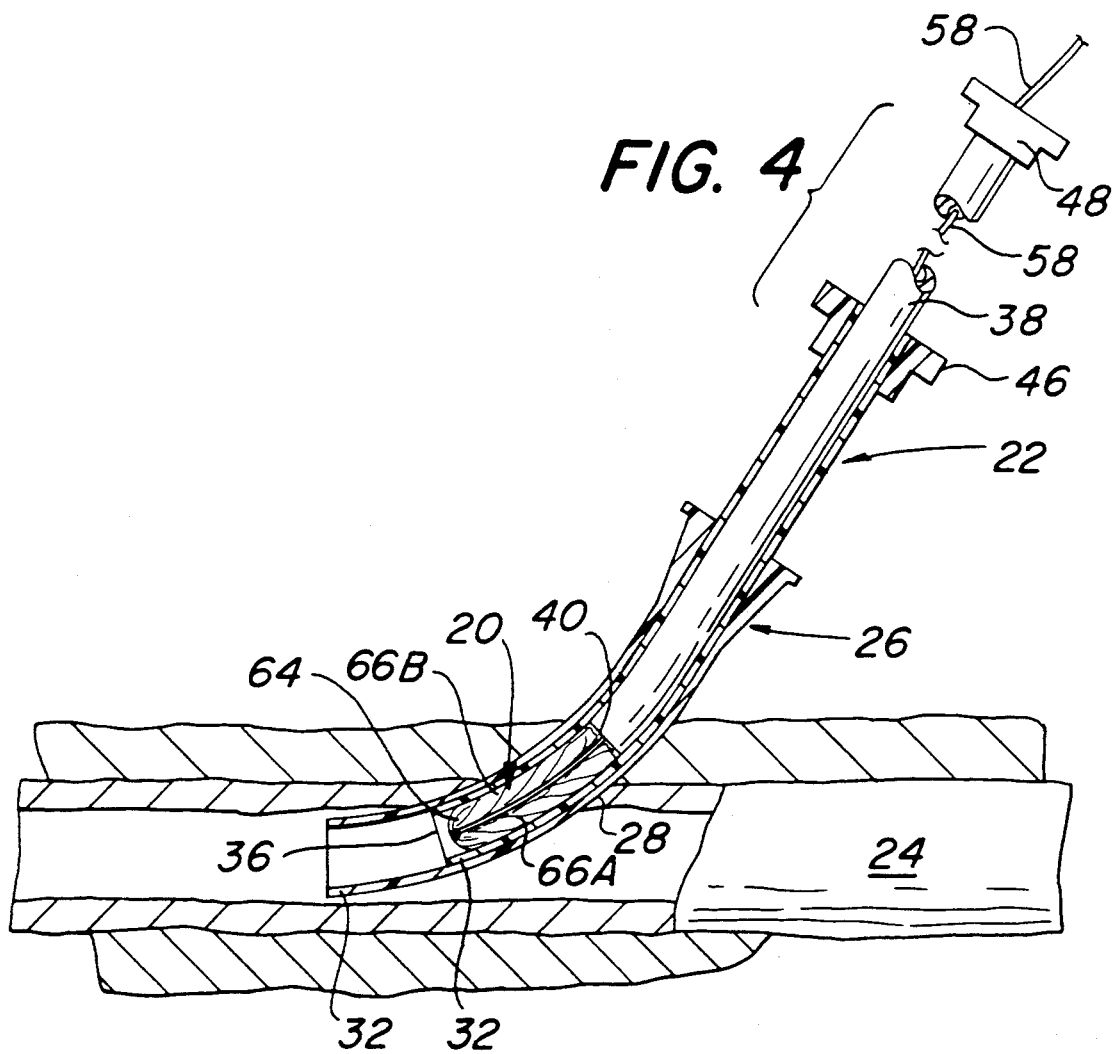
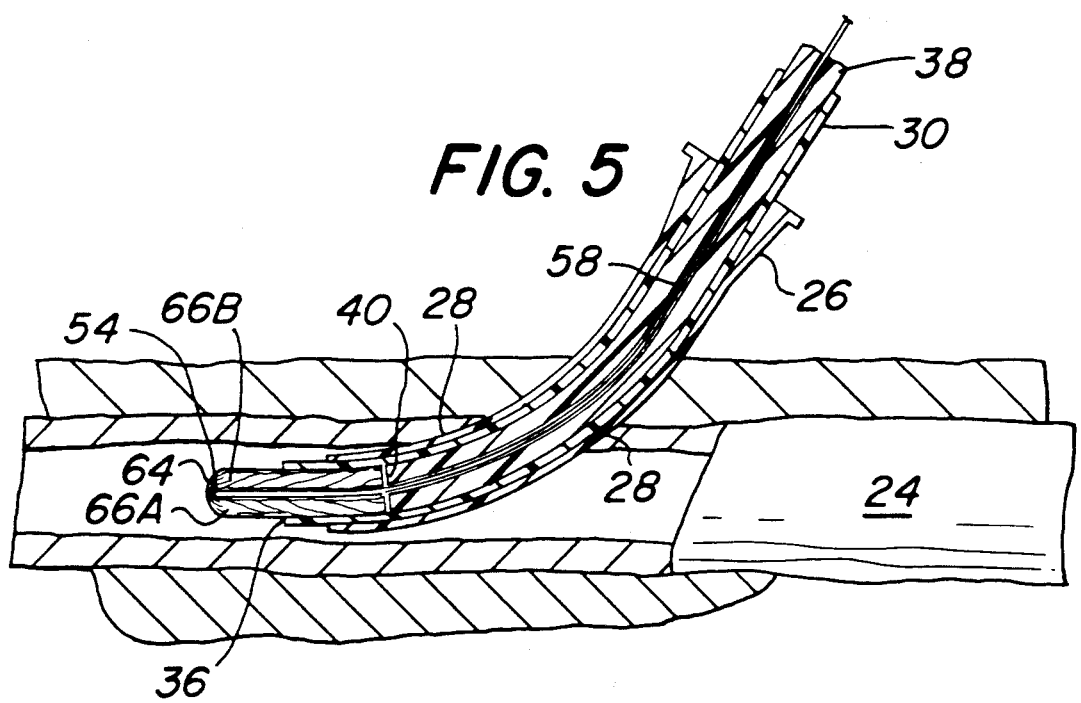

PLUG DEVICE FOR SEALING OPENINGS AND METHOD OF USE

This invention relates generally to medical devices and methods of use, and more specifically to devices and methods of use for sealing percutaneous openings or incisions in the body of a living being.

BACKGROUND OF THE INVENTION

In my U.S. Pat. Nos. 4,744,364 and 4,852,568, assigned to the same assignee as this invention, there is disclosed a device for sealing an incision or puncture in tissue separating one portion of the body of a living being from another portion, e.g., a puncture in a blood vessel, duct or lumen, of a living being. Also disclosed are methods of use of that device. The device basically comprises an elongated tubular body having an outlet at its distal end. The distal end of the device is arranged to be inserted, such as percutaneously, through the puncture. In the case where the puncture is an artery or other blood vessel, the outlet is inserted through the puncture so that it is located within the blood vessel's interior. An expandable closure is disposed within the device's tubular body and is formed so that it is held in a compact or compressed configuration within the tubular body. The tubular body also includes an ejector in the form of a plunger-like member arranged to force the closure out of the outlet into the portion of the being's body contiguous with the opening, e.g., within the interior of the blood vessel, whereupon the closure automatically expands to form an enlarged tissue engagement surface.

A retraction filament is secured to the closure to enable it to be pulled fully into the puncture after the device's tubular body has been withdrawn so that the engagement surface of the closure intimately engages the inner surface of the tissue contiguous with the puncture.

In accordance with one aspect of the disclosure of those patents, the filament is held taut or otherwise secured and placed on the patient's skin to hold the closure in position in the puncture. Preferably, the closure and filament are each formed of some biodegradable material to enable them to be left in place. When the closure is used for sealing punctures or incisions in blood vessels it is constructed so that when it is open (i.e., in its expanded state) and in place sealing the puncture it doesn't appreciably block the flow of blood through the blood vessel.

In my co-pending United States patent application, Ser. No. 194,641, filed on May 16, 1988, entitled Device For Sealing Percutaneous Puncture In A Vessel, there is disclosed a device for sealing a puncture or incision formed percutaneously in tissue separating two internal portions of the body of a living being and a method of use of that device. The device basically comprises a closure or plug formed of a material which when located within the puncture or incision expands automatically to engage the tissue contiguous therewith to seal the puncture and incision from the flow of body fluid therethrough. The closure disclosed in that application basically comprises a holding member, a filament, and a sealing member. The holding member is an elongated body, constructed like a toggle, and preferably formed of a biodegradable, thermoplastic polymer, such as polyglactide. The toggle is molded onto the distal end of the filament. The filament is also biodegradable, and preferably formed of polyglactide suture. The filament, being flexible, enables the toggle to pivot to various orientations with respect to it. The sealing member basically comprises a cylindrical plug, preferably formed of a compressed foam, which is highly absorbent and which when disposed within the body swells in excess of its compressed diameter.

The closure is arranged to be used by an instrument to place it within the puncture or incision to be sealed. The instrument includes a tubular member in which the closure is disposed so that the toggle is oriented with its longitudinal axis parallel to the longitudinal axis of the tubular member. When so disposed the toggle compresses the portion of the distal end of the sealing member. The filament extends backward from the toggle through the sealing member.

The instrument is introduced into the puncture or incision in the artery or any body tissue (e.g., the liver, gall bladder, lung, heart, etc.) until its outlet is at the desired position. In the case of sealing an artery, the outlet of the instrument is positioned so that it is within the artery. The instrument is then operated to expel the closure member from the tubular member. Once the closure is expelled, the instrument is held in this position for a short period of time to allow the foam at the tip of the closure, that is the distal end portion of the closure, to swell. This action effectively tilts the toggle. The instrument may then be withdrawn and the closure's filament retracted. This action pulls the closure's plug portion back, through the puncture or incision in the artery wall until its toggle portion engages the inner surface of the artery wall to stop further retraction. As the toggle comes into engagement with the arterial wall, it effects the compression of the distal end portion of the sealing member. Moreover, the proximal end portion of the sealing member extends into the puncture or incision in the subcutaneous tissue to a point closely adjacent the skin. These actions effectively seal the puncture or incision from the passage of blood therethrough.

Other alternative embodiments of a plug or closure are also disclosed in my aforementioned patent application. Those alternative embodiments basically comprise a preformed foam plug having an enlarged distal end portion serving as the holding member and a proximately located, rod-like portion serving as a sealing member. A retraction filament is secured to the sealing member. The closure is preferably formed of a dense collagen foam, with long collagen fiber reinforcements, so that it has a high expansion ratio (wet-to-dry) and good mechanical wet strength. Those alternative closures are also held within the instrument in a compressed state, with the holding portion located adjacent the instrument's outlet, and are inserted into the incision or puncture in the same manner as described heretofore. Once the closure is ejected out of the instrument, the holding portion of the closure swells upon contact with blood in the artery. The closure, now swollen, hangs up at the puncture or incision within the arterial wall, with the enlarged holding member portion engaging the inner surface of the interior wall and the sealing portion extending fully through the puncture or incision into the subcutaneous tissue. The filament is retracted to fully seat the closure in place so that the sealing portion extends fully through the puncture or incision in the arterial wall and with its proximal end located within the subcutaneous tissue closely adjacent the skin.

While the foregoing closures are generally suitable for their intended purposes, they still leave something to be desired from the standpoint of simplicity of construction and ease of use.

OBJECTS OF THE INVENTION

Accordingly, it is a general object of this invention to provide a device and methods of use which overcomes the disadvantages of the prior art.

It is a further object of this invention to provide a device and method of use for quickly, easily, and effectively sealing a puncture or incision in tissue separating one portion of the body of a living being from another portion.

SUMMARY OF THE INVENTION

These and other objects of this invention are achieved by providing a device and method of use for sealing a small incision or puncture in tissue separating one portion of the body of a living being from another portion thereof to prevent the flow of bodily fluid from the one portion to the other portion through the incision or puncture. The device is arranged to be used with an instrument which comprises a carrier in the form of a tubular member. The tubular member has a proximally located portion and a distally located portion. The latter includes an open free end arranged to be introduced through the incision or puncture. The proximately located portion of the tubular member is arranged to be located out of the body of the being when the distally located portion is extended through the incision or puncture.

The device basically comprises a plug made up of a cord-like member and a thin filament. The cord-like member comprises a resorbable material and is folded in two to form an apex portion and a pair of wing portions extending therefrom. The plug's filament is secured to the apex portion. The plug is arranged for location within the instrument's tubular carrier so that its apex portion is disposed adjacent the instrument's free end, and with its wing portions and its filament extending toward the proximally located portion of the instrument.

In accordance with one aspect of the method of this invention the plug means is arranged to be expelled partially from the tubular free end of the carrier so that its apex portion extends through the incision or puncture. After that is accomplished the filament is drawn in the proximal direction to cause the apex portion to engage the free end of the carrier to cause the cord-like member to form an expanded head having a peripheral, tissue-engagement surface. The plug is then drawn back through the incision or puncture so that the peripheral tissue engagement surface intimately engages the tissue contiguous with the incision or puncture.

In accordance with another aspect of the method of this invention the filament is secured to the apex portion of the cord and comprises first and second portions. The first portion of the filament is introduced into the proximal end of the carrier means' tubular member and drawn therethrough in a proximal direction to pull the plug therein and through the tubular member until the apex portion of the plug is located immediately adjacent the open free end of the tubular member, and with the second portion of the filament extending in a proximal direction from the plug and through the proximal portion of the tubular member. The first portion of the filament is then severed immediately adjacent the apex of the plug, whereupon the instrument is ready for insertion in the puncture or incision to expel the plug therefrom to seal that incision or puncture.

BRIEF DESCRIPTION OF THE DRAWINGS

Other objects and many of the attendant advantages of this invention will readily be appreciated as the same becomes better understood by reference to the following detailed description when considered in connection with the accompanying drawings wherein:

FIG. 1 is a side elevational view of the plug device of this invention;

FIG. 2 is a side elevational view, partially in section, showing an initial step of inserting the plug device shown in FIG. 1 into a portion of an instrument in preparation for its use;

FIG. 3 is a side elevational view, partially in section, similar to that of FIG. 1 and showing the final step readying the plug device and the instrument holding it for use to seal an incision or puncture.

FIG. 4 is a side elevational view, partially in section, showing the instrument having the plug device constructed in accordance with this invention therein being inserted into a conventional sheath extending through a percutaneous incision or puncture into an artery to effect the sealing of that incision or puncture;

FIG. 5 is a side elevational view, partially in section, similar to FIG. 4 and showing an intermediate step in the process of sealing the incision or puncture;

DETAILED DESCRIPTION OF THE PREFERRED EMBODIMENT

Figure 6:
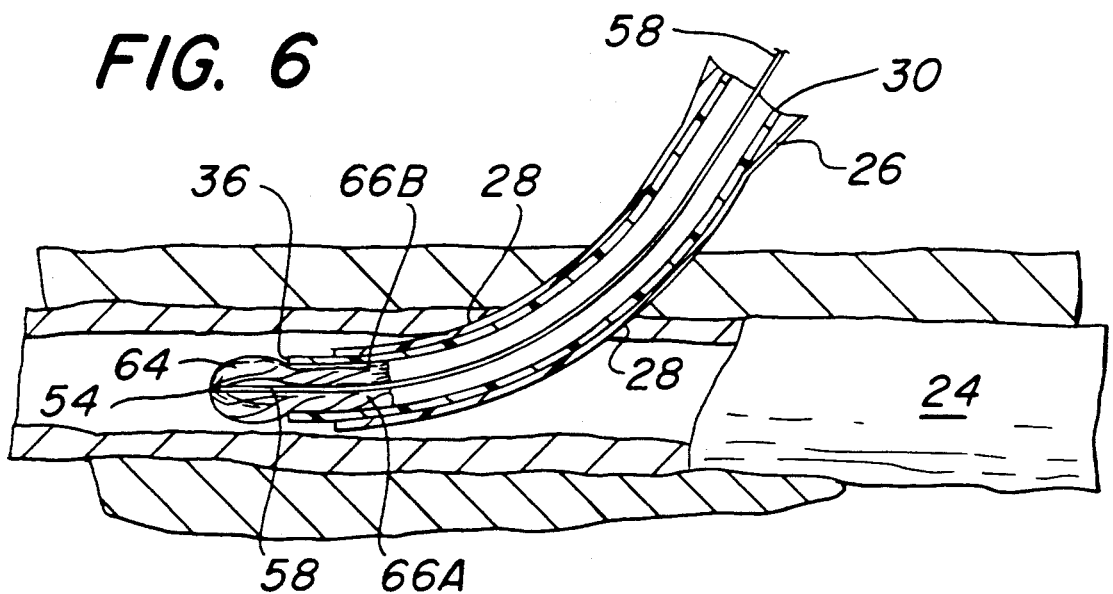
FIG. 6 is a side elevational view, partially in section, similar to FIG. 4 and showing a subsequent intermediate step in the process of sealing the incision or puncture.
Figure 7:
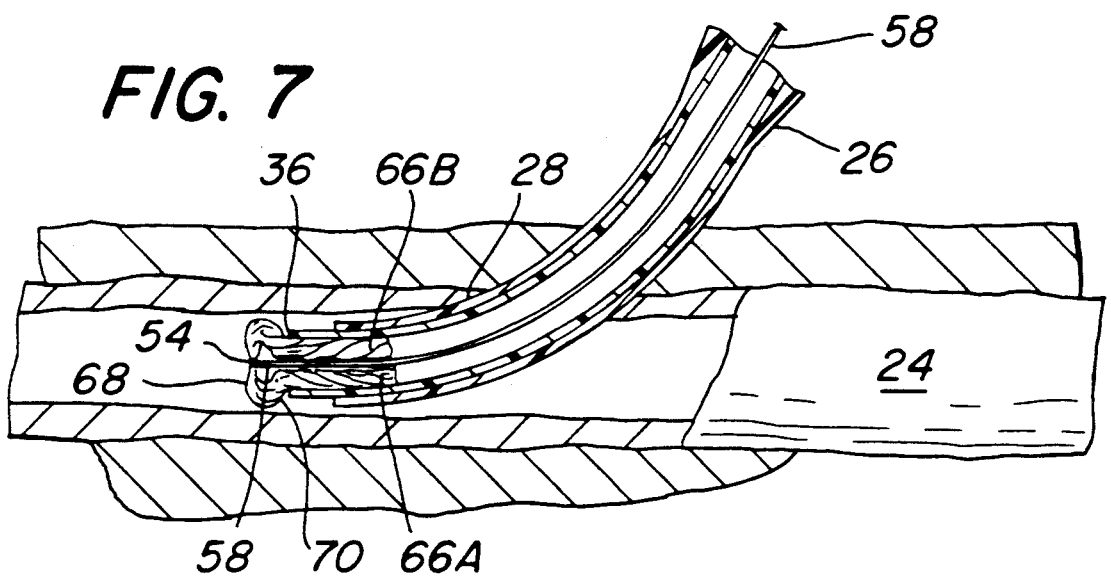
FIG. 7 is a side elevational view, partially in section, similar to FIG. 4 and showing a further subsequent intermediate step in the process of sealing the incision or puncture.

Referring now in greater detail to the various figures of the drawings wherein like reference characters refer to like parts, a plug device embodying the present invention is generally shown at 20 in FIG. 1. The device 20 is arranged to be used to effect the sealing of an incision or puncture or other small opening in any tissue separating two portions of the body of a living being to prevent liquid(s) or body fluid(s) to flow through the incision or puncture. The device 20 has particular utility when used in connection with intravascular procedures, such as angiographic dye injection, balloon angioplasty and other types of recanalizing of athlosclerotic arteries, etc. However, it is to be understood that while the description of the preferred embodiment device contained herein is directed to the closing off of percutaneous incisions or punctures in arteries, the device has much more wide-spread applications. Thus, the sealing of a percutaneous incision or puncture in an artery shown herein is merely exemplary.

In order to use the device to seal the incision or puncture, the device is arranged to be located within an introducing instrument 22 like that shown in FIG. 3 and which will be described in detail later.

Before describing the device 20 and the instrument 22 for inserting it to seal the incision or puncture, a brief description of a typical, conventional, intravascular surgical procedure, e.g., catheter instrumentation of an artery, utilizing a percutaneous incision or puncture will be given to best appreciate the features of the invention. In such a procedure a cannula of an instrument, such as an angiographic needle (not shown), is inserted percutaneously through the skin into the artery, such as the femoral artery 24 at the situs for the instrument's 22 insertion (See FIG. 4). The needle cannula is held in place and the flexible end of a mini-guidewire (not shown) is then passed through the cannula into the artery to the desired depth (i.e., longitudinal position therealong). Once the mini-guide wire is in place the needle cannula is removed, leaving the guidewire in place. A conventional introducing sheath 26 and an arterial dilator (not shown) are then passed over the guidewire, through the puncture or incision 28 and into the artery 24. The guidewire and then the dilator are removed leaving the sheath in place. The catheter (not shown) or other intravascular instrument (not shown) is then inserted through the introducer sheath 26 and threaded down the artery to the desired intravascular location, e.g., the situs of the athlosclerotic occlusion. Once the intravascular procedure (e.g., angioplasty) has been completed, the catheter is removed. Thereafter, the sheath is removed and the surgeon or other trained person applies digital pressure to the percutaneous puncture until hemostasis has occurred.

The device 20 effects the hemostatic closure of the percutaneous (or any other type of puncture, incision or opening) in the artery or any other tissue separating two portions of the body without necessitating the application of pressure thereto. Thus, once the catheter or intravascular instrument has been removed, but with the introducer sheath 26 left in place, the instrument 22 holding the device 20 of the subject invention is inserted through the sheath, into the artery 24 and operated to expel the device 20 into the artery 24.

As can be seen clearly in FIG. 1, the device 20 basically comprises a closure or plug, whose details will be described later, which is arranged to be drawn into the puncture or incision 28 to seal it. The introducer sheath 26 is then removed and the closure or plug left in place. Due to its construction the closure or plug is ultimately absorbed by the surrounding tissue.

Referring now to FIGS. 2 and 3, the details of instrument 22 will now be described. As can be seen the instrument 22 basically comprises a carrier in the form of a tubular body 30 having a distal end 32 and a proximal end 34. The distal end 32 forms a free end of the instrument and comprises an open outlet 36. The tubular body is preferably constructed of a sufficiently small outside diameter, e.g., 8F (French) and somewhat flexible material, such as polyethylene or polyvinyl chloride, to enable it to be inserted through the introducer sheath 26 into the artery 24, with the tubular body's outlet 36 within the artery 24 distally of the incision or puncture 28 as will be described later. A pusher member 38 is disposed within the tubular member 30. The pusher basically comprises an elongated, cylindrical rod-like member, having a free or distal end 40 and a proximal end 42. A central passageway 44 extends through the pusher. Preferably the pusher is also formed of a relatively flexible material, such as polyethylene or polyvinyl chloride, and is disposed within the interior of the tubular body as shown in FIG. 3 when the instrument is ready for use. The outside diameter of the pusher is slightly less than the inside diameter of the tubular body to enable the pusher to be manually moved, that is slid, down the longitudinal axis of the tubular body, to push or force the closure 20 out of the outlet 36, as will be described later.

The proximal end of the tubular member 30 includes a flange 46 and the proximal end 42 of the pusher 38 includes a similar flange forming a cap 48. The flanges 46 and 48 form portions to be gripped or engaged by the operator's fingers to enable the pusher to be moved (pushed) longitudinally down the tubular member to expel the closure 20, as will be described later.

Referring again to FIG. 1 it can be readily seen that the closure or plug 20 basically comprises a cord 50 and a filament 52. In accordance with one aspect of the preferred embodiment of the invention, the cord comprises a stranded yarn of plural fibers 50A of collagen or some other absorbable material. In particular one exemplary yarn consists of five strands 50A of 0.032 inch (0.81 mm) fibers which are twisted together. The filament 52 is secured to the cord 50 by wrapping it about the midsection 54 of the cord and knotting it thereat. This action forms a pair of filament sections, namely, 56 and 58, with section 56 forming a distally extending section with portion 58 forming a proximately extending portion.

As can be seen clearly in FIG. 2 the plug 20 is arranged to be inserted into the tubular member 30 of the instrument 22 as follows: the distally extending filament portion 56 is inserted through the open proximal end of the tubular member 30 and extended therethrough until its free end 60 extends out of the outlet 36 of the tubular member. The distally extending filament portion 56 is then pulled in the distal direction, like shown by arrow 62, whereupon the cord 50 of the closure 20 enters into the open proximal end of the tubular member. This action causes the cord to fold in half to form a leading or apex portion 64 and a pair of trailing, i.e., proximately extending, wing portions 66A and 66B. The distally extending filament portion 56 is then continued to be pulled in the proximal direction, thereby drawing the folded plug 20 down the tubular member 30 until its apex 64 is immediately adjacent the open end 36 of the tubular member 30. When the plug is in this position (shown in FIG. 3) the proximally extending filament portion 58 extends in the proximal direction from the folded cord 50 through the tube 30 and out its open proximal end. The pusher member 38 is then inserted within the tubular member 30. In particular, the free end of the proximally extending filament portion 58 is introduced into the distally located opening in the central passageway 44 of the pusher and threaded down the central passageway until it extends out of the opening at the flange or head 48 of the pusher. The pusher is then introduced into the proximately located opening in the tubular member and slid down the interior thereof in the distal direction until its 40 free end is located immediately adjacent the wings 66A and 66B of the plug 20. The distally extending filament portion 56 is then cut off or severed from the apex 36 of the cord immediately adjacent the apex. Once this latter action has been achieved the instrument 22 is ready for use.

Operation of the instrument 20 is best understood by reference to FIGS. 4-8 and is as follows: the instrument 20 is inserted within the introducer sleeve 26 so that the free end 32 of the tubular member 30 extends through the puncture or incision 28 like that shown in FIG. 4. The user then engages and pushes on the cap 48 of the pusher with his/her thumb while grasping the flange 46 of the tubular member between his/her fingers. This action slides the pusher in the distal direction within the tubular member 30 so that its free end 40 engages the end of the wing portions 66A and 66B of the plug to force the apex portion 64 of the plug out of the open free end 36 of the tubular member as shown in FIG. 5. The plug is left in this position for a few minutes, whereupon the portion extending into the artery expands slightly in the presence of the liquid, e.g., blood, etc., within the artery, as shown in FIG. 6.

The proximally extending filament portion 58 is then pulled in the proximal direction. This action causes the enlarged portion of the cord's apex to engage the free edge of the opening 36 of the tubular member 30 thereby further radially expanding and flattening that portion to form an enlarged or mushroom shaped head 68.

Figure 8:
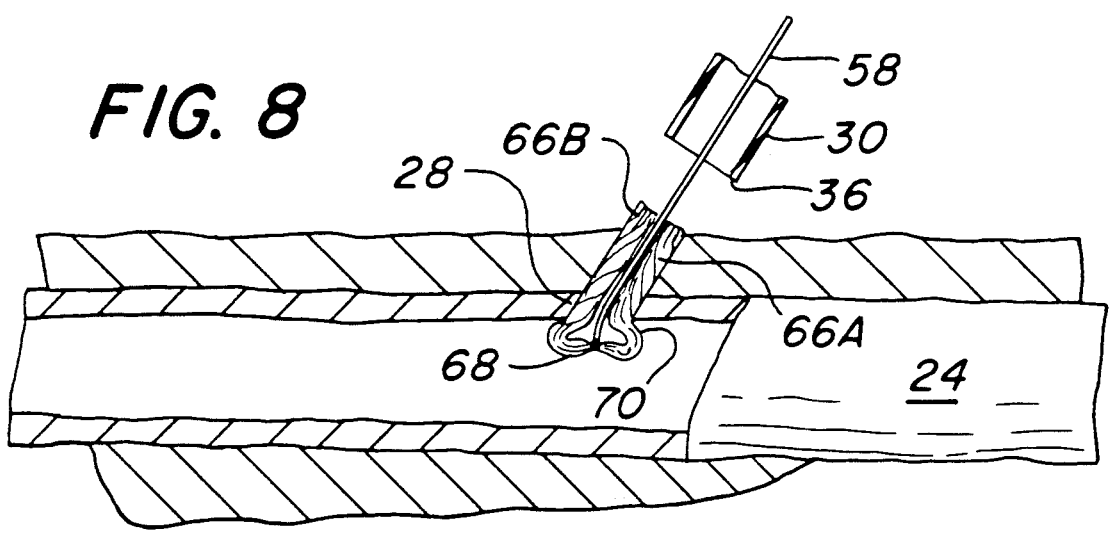
FIG. 8 is a side elevational view, partially in section, similar to FIG. 4 and showing the final step in the process of sealing the incision or puncture.

After the head 68 of the plug 20 has been expanded to its maximum diameter the introducer sleeve 26 is removed from the puncture or incision 28 and the instrument 22 is then withdrawn as shown in FIG. 8. This retraction action (i.e., the removal of the instrument from within the puncture or incision 28) causes the peripheral edge portions 70 on the underside of the enlarged head 68 of the plug to be drawn into close or intimate engagement with the tissue contiguous with the incision or puncture 28 to thereby seal that incision or puncture.

As can be seen in FIG. 8 with the closure in position the head 68 does not take up a substantial portion of the interior of the artery and thus does not block off or otherwise impede the flow of blood therethrough.

When the closure 20 of the subject invention is used to hemostatically seal a puncture or incision in an artery or other vessel, in order to minimize the risk of thrombosis the head of the closure which is exposed to the flow of blood through the artery may be coated with a non-thrombogenic material. Such a material can comprise a waxy coating, such as coconut oil, etc.

As mentioned earlier the cord 50 is formed of a resorbable, e.g., biodegradable, material. In accordance with the preferred embodiment of the invention, the filament 52 is also resorbable, and is preferably a suture of 3-0 size. These features enable the cord and filament to be left in place after hemostasis has occurred, since both will be absorbed by body's tissues thereafter. Accordingly, the plug does not have to be removed after having served its purpose.

Moreover, when the plug of the instant invention is used for sealing punctures or incisions in arteries a conventional clotting agent, such as tissue thromboplastin may be provided in the closure to accelerate hemostasis.

While the plug's cord has been described as comprising a stranded yarn of plural fibers such a construction is merely exemplary of various types of constructions. Thus, the "cord" may merely consist of a strip or bar of some resorbable material which is sufficiently flexible to fold over and form the heretofore described apex and wing portions.

As should be appreciated from the foregoing the plug device of the subject invention and its method of use enables the ready, effective and efficient sealing of punctures or incisions in body organs or tissue, be they blood vessels, other lumens, ducts, etc. For example, the device and its method of use can be used for the purpose of sealing percutaneous transhepatic punctures to preclude the risk of bile leakage into the peritoneum, via the liver puncture site. Moreover, the device and method of use can be used for sealing percutaneous incisions in the lung or heart, such as could result from a wound.

Without further elaboration the foregoing will so fully illustrate our invention that others may, by applying current or future knowledge, adopt the same for use under various conditions of service.

What is claimed is:

1. An instrument for sealing a small incision or puncture in tissue separating one portion of the body of a living being from another portion thereof to prevent the flow of bodily fluid from said one portion to said other portion through said incision or puncture, said instrument comprising plug means and carrier means, said carrier means comprising tubular means having a proximally located portion and a distally located portion, said distally located portion having an open free end arranged to be introduced through said incision or puncture, said proximately located portion being arranged to be located out of the body of said being when said distally located portion is extended through said incision or puncture, said plug means comprising strip means and thin filament means, said strip means being formed of a resorbable material and being folded in two to form an apex portion and a pair of wing portions extending therefrom, said filament means being secured to said apex portion, said plug means being arranged for location within said tubular means so that said apex portion is disposed adjacent said free end and with said wing portions and a portion of said filament means extending toward said proximal portion, said plug means being arranged to be expelled partially from said free end of said tubular means so that said apex portion extends through said incision or puncture, said portion of said filament means being arranged to be drawn in the proximal direction to cause said apex portion of said strip means to engage the free end of said tubular means to form an expanded head having a tissue engagement surface, said plug means then being arranged to be positioned so that said tissue engagement surface intimately engages the tissue contiguous with said incision or puncture.

2. The instrument of claim 1 wherein said strip means comprises a stranded yarn composed of plural fibers.

3. The instrument of claim 2 wherein said fibers are twisted together.

4. The instrument of claim 3 wherein said fibers are approximately 0.032 inch (0.81 mm) in diameter.

5. The instrument of claim 4 wherein said fibers comprise collagen.

6. The instrument of claim 4 wherein said filament means comprises a resorbable material.

7. The instrument of claim 6 wherein said filament means comprises a monofilament suture of 3-0 size.

8. The instrument of claim 1 wherein said strip means comprises collagen.

9. The instrument of claim 2 wherein said fibers comprise collagen.

10. The instrument of claim 2 wherein said fibers are approximately 0.032 inch (0.81 mm) in diameter.

11. The instrument of claim 1 wherein said filament means comprises a resorbable material.

12. The instrument of claim 9 wherein said filament means comprises a monofilament suture of 3-0 size.

13. The instrument of claim 1 wherein said carrier means additionally comprises pusher means to eject said plug means from said free end of said tubular means.

14. A plug for sealing a small incision or puncture in tissue separating one portion of the body of a living being from another portion thereof to prevent the flow of bodily fluid from said one portion to said other portion through said incision or puncture, said plug being arranged to be inserted into said incision or puncture by an instrument comprising carrier means, said carrier means comprising tubular means having a proximally located portion and a distally located portion, said distally located portion having an open free end arranged to be introduced through said incision or puncture, said proximately located portion being arranged to be located out of the body of said being when said distally located portion is extended through said incision or puncture, said plug comprising strip means and thin filament means, said strip means comprising a resorbable material and being folded in two to form an apex portion and a pair of wing portions extending therefrom, said filament means being secured to said apex portion, said plug being arranged for location within said tubular means so that said apex portion is disposed adjacent said free end and with said wing portions and a portion of said filament means extending toward said proximal portion, said plug being arranged to be expelled partially from said free end of said tubular means so that said apex portion extends through said incision or puncture, said portion of said filament means being arranged to be drawn in the proximal direction to cause said apex portion of said plug to engage the free end of said tubular means to form an expanded head having a tissue engagement surface, said plug then being arranged to be positioned so that said tissue engagement surface intimately engages the tissue contiguous with said incision or puncture.

15. The plug of claim 14 wherein said strip means comprises plural fibers.

16. The plug of claim 15 wherein said fibers are approximately 0.032 inch (0.81 mm) in diameter.

17. The plug of claim 16 wherein said filament means comprises a resorbable material.

18. The plug of claim 17 wherein said filament means comprises a monofilament suture of 3-0 size.

19. The plug of claim 15 wherein said fibers comprise collagen.

20. The plug of claim 14 wherein said fibers are twisted together.

21. The plug of claim 15 wherein said strip means comprises plural fibers which are twisted together.

22. The plug of claim 14 wherein said filament means comprises a resorbable material.

23. The plug of claim 22 wherein said filament means comprises a monofilament suture of 3-0 size.

24. A method of preparing an instrument for sealing a small incision or puncture in tissue separating one portion of the body of a living being from another portion thereof to prevent the flow of bodily fluid from said one portion to said other portion through said incision or puncture, said instrument comprising carrier means and plug means, said carrier means comprising a tubular member having a proximally located portion and a distally located portion, said distally located portion having an open free end arranged to be introduced through said incision or puncture, said proximately located portion being arranged to be located out of the body of said being when said distally located portion is extended through said incision or puncture, said plug means comprising strip means and thin filament means, said strip means being folded in two to form an apex portion and a pair of wing portions extending therefrom, said filament means being secured to said apex portion of said strip means and comprising a first and a second portion, said method comprising introducing said first portion of said filament means into said proximal end of said tubular member and drawing it therethrough in a proximal direction to pull said plug means therein and through said tubular member until the apex portion of said plug means is located immediately adjacent said open free end of said tubular member, with said second portion of said filament means extending in a proximal direction from said plug means and through said proximal portion of said tubular member, and then severing said first portion of said filament means immediately adjacent said apex of said plug means.

25. The method of claim 24 wherein said instrument additionally comprises a pusher member having a free end, said method additionally comprising the step of placing said pusher within said tubular member so that said free end of said pusher member is located immediately adjacent said plug means.

26. The method of claim 25 wherein said pusher member includes a passageway therethrough and wherein said method additionally comprises extending said second portion of said filament means through said passageway in said pusher member.

27. The method of claim 26 wherein said strip means is foldable and wherein said method additionally comprises folding said strip means as said plug means is pulled into said tubular member.

28. The method of claim 24 wherein said strip means is foldable and wherein said method additionally comprises folding said strip means as said plug means is pulled into said tubular member.

29. A method of using an instrument to seal a small incision or puncture in tissue separating one portion of the body of a living being from another portion thereof to prevent the flow of bodily fluid from said one portion to said other portion through said incision or puncture, said instrument comprising carrier means, plug means and pusher means, said carrier means comprising a tubular member having a proximally located portion and a distally located portion, said distally located portion having an open free end arranged to be introduced through said incision or puncture, said proximately located portion being arranged to be located out of the body of said being when said distally located portion is extended through said incision or puncture, said pusher means having a free end portion, said plug means comprising strip means and thin filament means, said strip means being folded in two to form an apex portion and a pair of wing portions extending therefrom, said filament being secured to said apex portion of said strip means and comprising a first portion and a second portion, said method comprising introducing said first portion of said filament into said proximal end of said tubular member and drawing it therethrough in a proximal direction to pull said plug means therein and through said tubular member until said apex portion of said plug means is located immediately adjacent said open free end of said tubular member, with said second portion of said filament means extending in a proximal direction from said plug means and through said proximal portion of said tubular member, severing said first portion of said filament means immediately adjacent said apex of said plug means, said pusher means being within said tubular member so that a free end portion of said pusher means is located adjacent said plug means, introducing said open free end of said distal portion of said tubular member within said incision or puncture, causing said pusher means to expel said plug means partially from said free end of tubular member so that said apex portion of said plug means extends through said incision or puncture, drawing on said second portion of said filament means in the proximal direction to cause said apex portion of said plug means to engage the free end of said tubular member to form an enlarged head having a tissue engagement surface, and drawing said plug means in the proximal direction so that said tissue engagement surface of said plug means intimately engages the tissue contiguous with said incision or puncture.

30. The method of claim 29 wherein said instrument additionally comprises the step of allowing said apex portion of said strip means which is extended through said incision or puncture to automatically expand somewhat in the presence of body liquid located at the situs of said incision or puncture and after said apex portion has expanded somewhat then drawing on said second portion of said filament means in the proximal direction to form said enlarged head.

31. The method of claim 30 wherein said plug means comprises at least one resorbable material, and wherein said method additionally comprises leaving said plug means within said incision or puncture until it is absorbed by the body of said being.

32. The method of claim 30 wherein said tissue engagement surface of said plug means is brought into intimate engagement with the tissue contiguous with said incision or puncture by the withdrawal of said instrument from within said incision or puncture.

33. The method of claim 29 wherein said plug means comprises at least one resorbable material, and wherein said method additionally comprises leaving said plug means within said incision or puncture until it is absorbed by the body of said being.

34. The method of claim 29 wherein said tissue engagement surface of said plug means is brought into intimate engagement with the tissue contiguous with said incision or puncture by the withdrawal of said instrument from within said incision or puncture.

* * * * *